United States Patent [19]

Nakamura

[11] Patent Number: 5,463,976
[45] Date of Patent: Nov. 7, 1995

[54] PRODUCTION OF CRYSTALS OF DIESTER PHOSPHATE MONOPOTASSIUM SALT

[75] Inventor: Masayuki Nakamura, Himeji, Japan

[73] Assignee: Senju Pharmaceutical Co., Ltd., Osaka, Japan

[21] Appl. No.: 412,886

[22] Filed: Mar. 29, 1995

[30] Foreign Application Priority Data

Apr. 1, 1994 [JP] Japan .................. 6-065133

[51] Int. Cl.$^6$ .................. C30B 29/54
[52] U.S. Cl. .................. 117/68; 117/70; 117/925
[58] Field of Search .................. 117/68, 70, 925

[56] References Cited

U.S. PATENT DOCUMENTS

| | | | |
|---|---|---|---|
| 3,951,825 | 4/1976 | Carver | 252/8.7 |
| 4,293,305 | 10/1981 | Wilson | 8/115.6 |
| 4,394,126 | 7/1983 | Wilson | 8/115.6 |
| 4,426,297 | 1/1984 | Wilson | 252/8.6 |

FOREIGN PATENT DOCUMENTS 61-225372  10/1986  Japan .

*Primary Examiner*—Robert Kunemund
*Attorney, Agent, or Firm*—Wenderoth, Lind & Ponack

[57] ABSTRACT

A method for producing crystals of a diester phosphate monopotassium salt, comprising (a) reacting the diester phosphate of the formula (I)

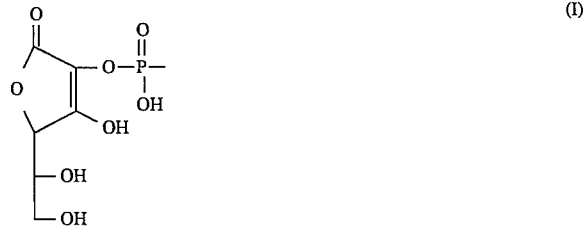
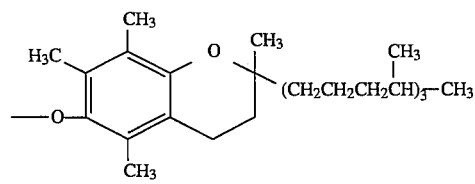

with potassium hydroxide in a solvent selected from the group consisting of isopropyl alcohol, methylene chloride and chloroform and (b) allowing crystals of the diester phosphate monopotassium salt to precipitate out. The EPC-K crystals produced by the production method of the present invention have extremely fine purity and crystal appearance. Accordingly, the present invention is advantageous in that provision of pharmaceutical preparation superior in efficacy, safety and stability has been made possible.

4 Claims, No Drawings

PRODUCTION OF CRYSTALS OF DIESTER PHOSPHATE MONOPOTASSIUM SALT

FIELD OF THE INVENTION

The present invention relates to a method for producing, at high purity, crystals of the diester phosphate monopotassium salt of the formula (II)

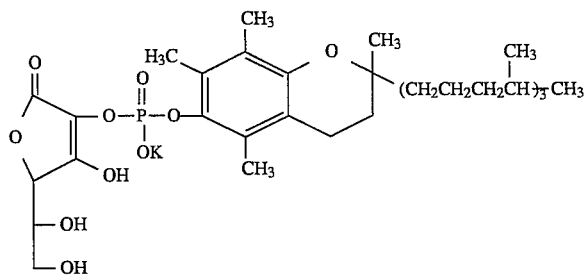

(II)

which are useful for the prophylaxis and treatment of cataract, circulatory organ disorders, climacteric disturbance and so on, or as anti-inflammatory agents.

BACKGROUND OF THE INVENTION

A diester phosphate of the formula (I)

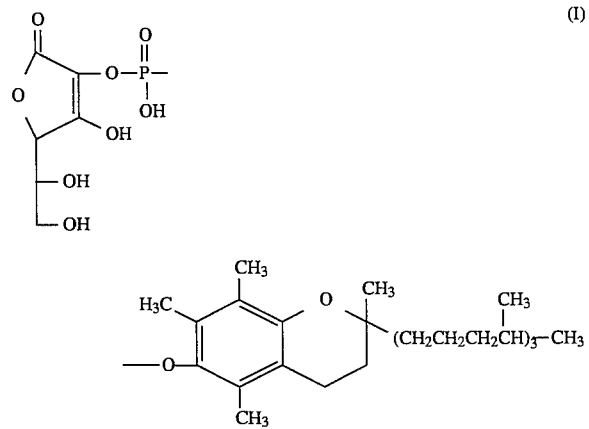

(I)

(hereinafter referred to as EPC) shows superior crystallinity when converted to a salt, which is typically exemplified by a potassium salt.

Crystals of EPC monopotassium salt (hereinafter referred to as EPC-K) show less moisture absorption and are stabler than the crystals of EPC dipotassium salt (hereinafter referred to as EPC-D) and a mixture of the both salts (hereinafter referred to as EPC-KM). In addition, the surface activity of EPC-K crystals is weaker than that of EPC-D crystals or EPC-KM crystals, thus causing less mucosal irritations. Moreover, EPC-K crystals show stronger antioxidative activity, which forms the basis for their pharmacological activity, than EPC-D crystals and EPC-KM crystals.

Therefore, crystals having the highest possible EPC-K crystal content are desirable from the aspects of efficacy, stability and safety.

However, there has been conventionally made no attempt to obtain high purity EPC-K crystals, and as far as the present inventor knows, there exists no proposition to selectively produce EPC-K crystals.

It is therefore an object of the present invention to provide a method for producing high purity EPC-K crystals, whereby to provide crystals superior in efficacy, safety and stability.

SUMMARY OF THE INVENTION

According to the present invention, it has now been found that EPC-K crystals having high purity and superior crystal appearance can be obtained by reacting EPC and potassium hydroxide in a solvent selected from isopropyl alcohol, methylene chloride and chloroform, and allowing the crystals of the diester phosphate monopotassium salt to precipitate out.

That is, the present invention relates to a method for producing crystals of the diester phosphate monopotassium salt, comprising reacting EPC and potassium hydroxide in a solvent selected from isopropyl alcohol, methylene chloride and chloroform, and allowing the crystals of the diester phosphate monopotassium salt to precipitate out.

DETAILED DESCRIPTION OF THE INVENTION

In the production method of the present invention, isopropyl alcohol, methylene chloride or chloroform is used as a solvent. Preferable solvent is methylene chloride.

EPC is generally dissolved in the above-mentioned solvent and applied to the method of the present invention. The solvent is generally used in an amount of 30–200 ml, preferably 40–60 ml per 10 g of EPC. When the solvent is used in the above-mentioned range, the purity of the EPC-K crystals and the appearance of the crystals obtained become fine.

Potassium hydroxide is generally used as an ethanol solution for the production method of the present invention. The concentration of the ethanol solution of potassium hydroxide is generally 0.1–3N, preferably 0.5–1.5N and more preferably about 1N. When the concentration of the ethanol solution of potassium hydroxide is in the above-mentioned range, the purity of the EPC-K crystals and the appearance of the crystals obtained become fine.

According to the production method of the present invention, EPC-K crystals are obtained by allowing EPC-K crystals to precipitate out from the reaction mixture of the above-mentioned solvent.

During precipitation, the pH of the reaction mixture is preferably adjusted to 1.0–3.0, preferably 1.5–2.5 and more preferably about 2, and cooling temperature is adjusted to −5° C. to 5° C., preferably −2° C. to 2° C. When the pH and the cooling temperature are in the above-mentioned range, the purity of the EPC-K crystals and the appearance of the crystals obtained become fine.

The starting material EPC is a compound known per se and can be produced by a method known per se. For example, EPC can be produced by the following reaction route.

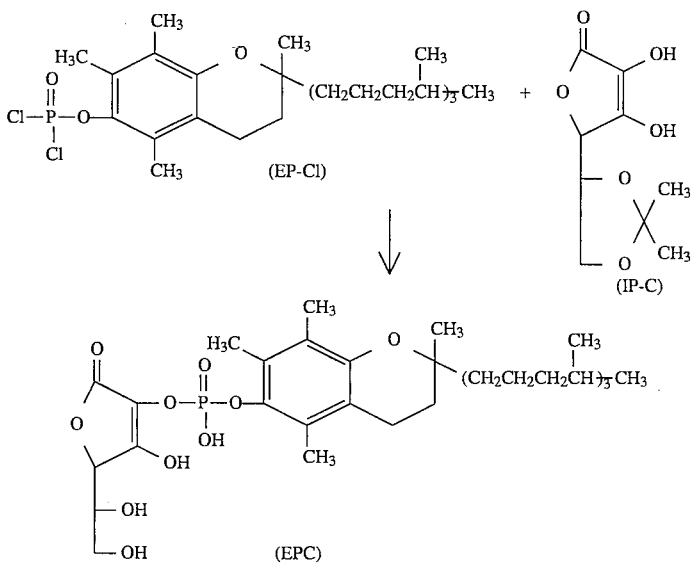

The EPC-K crystals thus obtained can be prepared into an appropriate pharmaceutical preparation such as injection, eye drop, tablet, capsule, ointment, cream and cataplasm by a method known per se.

The above-mentioned preparation may contain various pharmaceutically acceptable additives such as preservative, excipient, non-ionic surfactant, coloring agent and so on, to the extent that the object of the present invention is not impaired.

The present invention is described in more detail in the following by way of Examples and Comparative Examples.

Example 1

IP-C (47.4 g) was added to tetrahydrofuran (120 ml) to give a suspension, and pyridine (21.7 g) was added thereto. EP-Cl (60.0 g) was dissolved in tetrahydrofuran (120 ml) and dropwise added to the above-mentioned IP-C suspension at 10°–30° C. The mixture was stirred at said temperature for 2.5 hours. After the completion of the reaction, the mixture was washed with dilute hydrochloric acid (12 ml) and tetrahydrofuran was distilled away under reduced pressure. Dilute hydrochloric acid (90 ml) was added to the residue and the mixture was stirred at 20°–30° C. for 3 hours for hydrolysis. The mixture was extracted with ethyl acetate (360 ml) and the organic layer was washed with saturated brine (120 ml) and dried over anhydrous magnesium sulfate. Ethyl acetate was distilled away under reduced pressure. The residue (60 g) was dissolved in methylene chloride (240 ml) and the mixture was adjusted to pH 2.0 with a 1N potassium hydroxide/ethanol solution with stirring. The mixture was cooled to 4° C. and stirred for about 12 hours to allow precipitation. The precipitated crystals were collected by filtration, washed with ethanol (60 ml) and further washed with ethanol (120 ml) with stirring for 20 minutes, and dried under reduced pressure at 55° C. to give EPC-K crystals.

Elemental analysis Calculated: C,59.47; H,7.98 Found: C,59.22; H,7.69

$^1$H-NMR (270 MHz, CD$_3$OD) δ: 0.84–0.89 (m, 12H, —CH$_3$×4), 1.10–1.60 (m, 21H, —CH$_2$—×9, —CH—×3), 1.21 (s, 3H, —CH$_3$), 1.78 (t, 2H, —CH$_2$—), 2.04 (s, 3H, —CH$_3$), 2.19 (s, 3H, —CH$_3$), 2.23 (s, 3H, —CH$_3$), 2.58 (t, 2H, —CH$_2$—), 3.65 (d, 2H, —CH$_2$—), 3.85 (m, 1H, —CH—), 4.75 (d, 1H, —CH—) MS (m/z): 669 [M-K+2H]$^+$, 707 [M+H]$^+$, 745 [M+K]$^+$

The purity (by HPLC) and appearance of said crystals were examined, the results of which are shown in Table 1.

HPLC was performed under the following conditions. Mobile phase; methanol:acetonitrile:water (50:40:5), pH 4 (phosphate buffer), column; YMC Pack AL-314, column temperature 40° C., measurement wavelength 225 nm Examples 2–7, Comparative Examples 1–5

In the same manner as in Example 1, except that precipitation solvent, pH, cooling temperature and solvent amount were changed to those shown in Table 1, EPC-K crystals were produced. The purity and appearance of the crystals were determined, the results of which are shown in Table 1.

TABLE 1

| | Precipitation solvent | pH | Cooling temperature(°C.) | Solvent amount* (ml) | Purity (%) | Appearance |
|---|---|---|---|---|---|---|
| Ex. 1 | methylene chloride | 2 | 4 | 40 | 98.9 | white |
| Ex. 2 | isopropyl alcohol | 2 | 4 | 60 | 98.5 | white |
| Ex. 3 | chloroform | 2 | 4 | 60 | 98.9 | white |
| Com. Ex. 1 | ethyl acetate | 2 | 4 | 60 | 94.8 | yellow white |
| Com. Ex. 2 | ethanol | 2 | 4 | 60 | 94.3 | yellow white |
| Com. Ex. 3 | methanol | 2 | 4 | 60 | no crystal precipitated | |

TABLE 1-continued

| | Precipitation solvent | pH | Cooling temperature(°C.) | Solvent amount* (ml) | Purity (%) | Appearance |
|---|---|---|---|---|---|---|
| Com. Ex. 4 | toluene | 2 | 4 | 60 | | crystals unobtainable by filtration |
| Com. Ex. 5 | hexane | 2 | 4 | 60 | | crystals unobtainable by filtration |
| Ex. 4 | methylene chloride | 2 | −4 | 60 | 98.9 | white |
| Ex. 5 | methylene chloride | 2 | −20 | 60 | 98.5 | yellow white |
| Ex. 6 | methylene chloride | 2 | 4 | 60 | 98.9 | white |
| Ex. 7 | methylene chloride | 2 | 4 | 50 | 98.8 | white |

Note: *The solvent amount is the amount per 10 g of the diester phosphate.

The EPC-K crystals produced by the production method of the present invention have extremely fine purity and crystal appearance. For example, their purity is not less than 98%, preferably not less than 98.5%.

Accordingly, the present invention is advantageous in that provision of pharmaceutical preparation superior in efficacy, safety and stability has been made possible.

What is claimed is

1. A method for producing crystals of a diester phosphate monopotassium salt, comprising (a) reacting a diester phosphate of the formula (I)

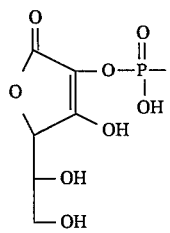

(I)

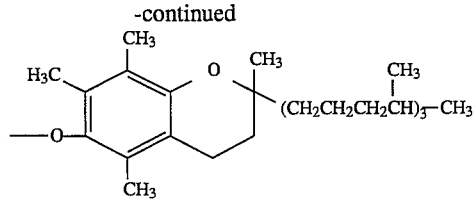

with potassium hydroxide in a solvent selected from the group consisting of isopropyl alcohol, methylene chloride and chloroform, and (b) allowing crystals of the diester phosphate monopotassium salt to precipitate out.

2. The method of claim 1, wherein the potassium hydroxide is used for the reaction as an ethanol solution.

3. The method of claim 1, wherein the crystals of the diester phosphate monopotassium salt are precipitated under at least one condition selected from (1) the solvent amount being 30–200 ml per 10 g of the diester phosphate, (2) pH of 1.0–3.0, and (3) cooling temperature of −5° C. to 5° C.

4. The method of claim 2, wherein the crystals of the diester phosphate monopotassium salt are precipitated under at least one condition selected from (1) the solvent amount being 30–200 ml per 10 g of the diester phosphate, (2) pH of 1.0–3.0, and (3) cooling temperature of −5° C. to 5° C.

* * * * *